United States Patent
Klein et al.

(10) Patent No.: US 9,039,734 B2
(45) Date of Patent: May 26, 2015

(54) IMPLANTABLE BIODEGRADABLE WOUND CLOSURE DEVICE

(71) Applicants: Michael Sigmund Klein, Salinas, CA (US); Charles Eichhorn Witherell, Salinas, CA (US)

(72) Inventors: Michael Sigmund Klein, Salinas, CA (US); Charles Eichhorn Witherell, Salinas, CA (US)

(73) Assignee: Capiq, Inc, Los Altos, CA (US)

( * ) Notice: Subject to any disclaimer, the term of this patent is extended or adjusted under 35 U.S.C. 154(b) by 156 days.

(21) Appl. No.: 13/783,342

(22) Filed: Mar. 3, 2013

(65) Prior Publication Data

US 2014/0081319 A1    Mar. 20, 2014

Related U.S. Application Data

(62) Division of application No. 12/758,027, filed on Apr. 11, 2010, now Pat. No. 8,506,593.

(51) Int. Cl.
*A61B 17/08* (2006.01)
*A61B 17/00* (2006.01)

(52) U.S. Cl.
CPC ... *A61B 17/0057* (2013.01); *A61B 2017/00637* (2013.01); *A61B 2017/00646* (2013.01)

(58) Field of Classification Search
CPC ............... A61B 17/0057; A61B 2017/0057; A61B 2017/00575; A61B 2017/00606; A61B 2017/00615; A61B 2017/00637; A61B 17/688; A61B 2017/00646; A44B 1/30

USPC ................. 606/153, 154, 157, 158, 213, 215, 606/301–310, 313, 314, 319, 320, 322, 323, 606/326, 327, 328; 24/94–96, 105, 289, 24/290, 453, 458, 581.11; 623/23.72
See application file for complete search history.

(56) References Cited

U.S. PATENT DOCUMENTS

| | | | | |
|---|---|---|---|---|
| 570,872 | A * | 11/1896 | Gardner | 24/105 |
| 1,026,017 | A * | 5/1912 | Anderson | 24/114.8 |
| 1,060,134 | A * | 4/1913 | Schmidt | 24/706.5 |
| 1,233,455 | A * | 7/1917 | Doucette | 24/105 |
| 2,174,521 | A * | 10/1939 | Lancaster | 24/105 |
| 3,494,246 | A * | 2/1970 | Hensley | 411/362 |
| 3,839,297 | A | 10/1974 | Wasserman | |
| 4,523,591 | A | 6/1985 | Kaplan | |
| 4,950,258 | A | 8/1990 | Kawai | |
| 5,366,460 | A | 11/1994 | Eberbach | |
| 6,120,539 | A | 9/2000 | Eldridge | |
| 6,210,539 | B1 | 4/2001 | Tanaka | |
| 6,241,768 | B1 | 6/2001 | Agarwal | |
| 7,189,024 | B2 * | 3/2007 | Cameron | 403/306 |
| 7,788,772 | B2 * | 9/2010 | Dandurand | 24/105 |
| 8,096,023 | B2 * | 1/2012 | Orza | 24/104 |
| 2003/0181988 | A1 | 9/2003 | Rousseau | |
| 2006/0015142 | A1 | 1/2006 | Malazgirt | |
| 2006/0282105 | A1 | 12/2006 | Palmer et al. | |
| 2009/0198260 | A1 | 8/2009 | Ford et al. | |

\* cited by examiner

*Primary Examiner* — Thomas McEvoy
(74) *Attorney, Agent, or Firm* — Michael Toback

(57) ABSTRACT

A biodegradable device for maintaining the alignment of the edges of a trocar defect, consisting of two bases joined by a connector, a first base to be positioned below the defect and a second base above. The first base has a threaded hole from its upper surface but not through the lower surface. The connector attached to the bases such that there is a hole aligned with the threaded hole in the first base allowing a device to mate with the threads in the first base. The second base has a hole aligned with the hole in the connector and wide enough to allow a device to mate with the threads in the first base. The device is arranged so the distance between the lower surface of the second base and upper surface of the first base holds but does not compress the fascia around the trocar defect.

18 Claims, 15 Drawing Sheets

IMPLANTABLE BIODEGRADABLE WOUND CLOSURE DEVICE

This patent is a divisional of "An Implantable Biodegradable Wound Closure Device and Method", filed on Apr. 11, 2010 as U.S. application Ser. No. 12/758,027.

BACKGROUND OF THE INVENTION

Field of the Invention

The present invention generally relates to a wound closure device that is used to repair the defect typically left in the fascia layer during laparoscopic surgery by an instrument called a trocar.

Laparoscopic surgery was introduced as an alternative to open surgical methods. Also referred to as minimally invasive surgery, the technique allows for small incision access to the intra-abdominal cavity. The approach utilizes specialized equipment for the purposes of inflating the abdominal cavity with gas, deploying and exchanging instruments during the operation, and real time imaging with a videoscopic camera.

A laparoscopic trocar is a surgical device used for laparoscopic procedures to pierce and access the wall of an anatomical cavity, thereby forming a passageway providing communication with the inside of the cavity. Other medical instruments such as videoscopes and operating instruments can thereafter be inserted through the passageway to perform various medical procedures within the anatomical cavity.

When the procedures are over, the laparoscopic trocar is removed, leaving a residual defect in the fascia-peritoneal layer. Laparoscopic trocars are typically 5-15 mm in diameter. Generally, any port size larger than 5 mm should be closed because of the risk of hernias. The defect is located deep in the abdominal wall, making it difficult to view.

Trocar site herniation is a recognized complication of laparoscopic surgery. Omental, and sometimes intestinal, herniation with incarceration and obstruction has been documented in recent surgical literature, occurring particularly at any trocar insertion site larger than 5 mm that was not sutured at operation. The necessity to perform fascial closure of any trocar insertion site larger than 5 mm has now been established and is routinely practiced worldwide.

However, the conventional closure of such a trocar site fascial defect is often technically difficult, frustrating, indefinitely successful, and even sometimes dangerous due to the limited size of skin incision, the depth of the subcutaneous fatty layer, and necessity of blind manipulation. Moreover, the suturing that involves placement of deep blind sutures after the abdomen has been decompressed is a dangerous manipulation that surgeons tend to avoid.

A number of techniques and instruments have been suggested to facilitate a safe and secure closure of the fascial defect through the tiny skin opening. Many of these repairs include passing in any way a suture from one side of the trocar wound to the other, and its ligation. For this purpose either a heavy needle or a variety of straight needles through which sutures are passed have been used. Problems arise as both sides of the defect may not be sutured. Also, in overweight and obese patients with thick abdominal walls, reliable fascia closure is very difficult to achieve. This results in a delayed hernia formation such as an incarcerated or symptomatic hernia. The literature shows as much as a 6% overall hernia complication rate, resulting in reoperation, rehospitalization, and extended disability. In the best case this results in the need for an elective repair, resulting in rehospitalization.

Although as easy and quick methods, these suturing techniques require positioning of the camera and graspers, visualization of the needles during their entrance into the peritoneal cavity, feeding of the graspers or suture passers with the suture loop, all of which are repeated once to thrice for every trocar defect. Any of these suturing techniques are not only time and effort consuming, but also require sophisticated laparoscopic talent and coordination. As more defects at various sites in the abdominal wall are to be closed after advanced laparoscopic operations, the laparoscopic procedures that support the suturing techniques become more complicated and complex. The above-mentioned suturing techniques would therefore be not that easy and quick.

Techniques using such instruments as the Carter-Thomason or Riza-Ribe® needles work by adding a catch onto the end of a needle assembly to catch a free floating suture. To facilitate the closure of the fascia defects of a trocar entry site greater than 5 mm, the surgeon places the upper end of a dissecting forceps through the fascial defect and tilts it so that the peritoneum comes into contact with its flat surface. An assistant retracts the skin and subcutaneous tissue and the needle with the appropriate suture material is then used to take a stitch through the fascia under direct vision. The sharp end of the needle is prevented from coming into contact with any deeper structure as it slides on the flat surface of the dissecting forceps. The stitch is then pulled up to lift the edge of the fascia and the needle is passed from the opposite edge of the fascia in the same manner and then the suture is ligated.

Moreover, a series of manipulations is needed to complete a single suturing. The conventional suturing technique involves much traumatic manipulation including pushing, pulling and retraction of the wound, and insertion and extraction of needles. Most of the time the needle is passed twice, and sometimes more (as depicted in Petrakis' technique). As manipulation in the wound increases, the inflammation and risk of ensuing infection rise considerably. The edema and the collection of seroma and hematoma at the wound further cause dehiscence and hernia formation on a long-term basis.

Excessive traumatic manipulation and suturing with heavy sutures oppose the "minimal damage" basis of laparoscopic surgery. The patients are subject to pain and complications at their trocar sites in the postoperative period. The problems associated with the repair of trocar wound would be annoying to the patient as he (or she) is discharged on the first or second postoperative day. The problems of the wound would cause the patient to refer back to the institution.

Any of these suturing techniques are to be done under direct vision. It is however impossible to repair the last trocar wound under direct vision. Unless a 0.5 cm scope is used, the last large trocar site can only be closed with conventional blind sutures. This is because at the conclusion of a typical multiport laproscopy procedure, all the ports are removed simultaneously and positive intra-abdominal pressure is lost immediately. The abdominal wall returns to a flat configuration, and the 10-12 mm trocar port incisions are then individually dosed. Therefore, there is no visibility on the surgeon's part. For a regular laparoscopic cholecystectomy, the surgeon can only repair the first of two large trocar defects under direct vision, and only then if he uses intracorporeal suturing, which is rarely performed because of the levels of skill and expertise required. In any case, he must close the last one blindly.

No matter which suturing technique or needle is used, it is not possible to eliminate the trocar site hernias completely. As described in Malazgirt (US patent application, pub #20060015142 published Jan. 19, 2006), the current incidence is reportedly between 0.77-3%. As complex Laparoscopic surgery becomes more common, the incidence of this complication increases. The reported rates of hernia show that there is not yet any superior method in the safe closure of the trocar fascial defect.

Eldridge and Titone (U.S. Pat. No. 6,120,539 Issued Sep. 19, 2000) proposed a prosthetic repair fabric constructed from a combination of non-absorbable tissue-infiltratable fabric which faces the anterior surface of the fascia and an adhesion-resistant barrier which faces outward from the fascia. This prosthetic requires the use of sutures to hold it in place.

Eberbach (U.S. Pat. No. 5,366,460 Issued Nov. 22, 1994) proposed the use of a non-biodegradable fabric-coated loop inserted through the defect into the fascia wall, pressing against the posterior fascia wall from the intra-abdominal pressure.

Agarwal et al (U.S. Pat. No. 6,241,768 Issued Jun. 5, 2001) proposed a prosthetic device made of a biocompatible non-biodegradable mesh, which sits across the fascia defect using the abdominal pressure to hold it in place.

Rousseau (Pat Pub#20030181988) proposed a plug made of biocompatible non-biodegradable material which covers the anterior side of the fascia, the defect, as well as the posterior side of the fascia.

Malazgirt (Pat Pub#20060015142) proposed a plug/mesh non-biodegradable combination for repair of large trocar wounds. It is stated that it requires at least a "clean flat area around with a radius of 2.5 cm", and requires staples to hold it in place.

Ford and Torres (Pat Pub#20060282105) proposed a patch with a tether or strap, all made of non-biodegradable biocompatible material placed against the anterior wall of the fascia defect.

SUMMARY

A biodegradable device for maintaining the alignment of the edges of a trocar defect, consisting of two bases joined by a connector, a first base to be positioned below the defect and a second base above. The first base has a threaded hole from its upper surface but not through the lower surface. The connector attached to the bases such that there is a hole aligned with the threaded hole in the first base allowing a device to mate with the threads in the first base. The second base has a hole aligned with the hole in the connector and wide enough to allow a device to mate with the threads in the first base. The device is arranged so the distance between the lower surface of the second base and upper surface of the first base holds but does not compress the fascia around the trocar defect.

DETAILED DESCRIPTION OF PREFERRED EMBODIMENTS

Figure 1:
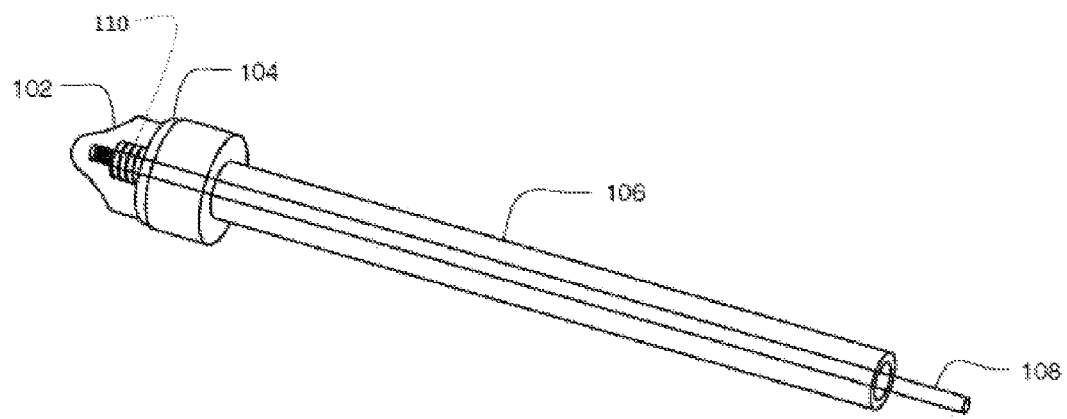
FIG. 1 shows a transparent view of the device at the end of the compression process in accordance with one or more embodiments of the present invention.

FIG. 1 shows a transparent view of an embodiment of the insertion tool, compression tool, and the wound closure device. The wound closure device consists of a subfascial button 102, screw 110, and superfascial button 104. In one or more embodiments, the insertion tool consists of a central insertion stem 108. In one or more embodiments, the compression tool consists of an outer tube 106.

In one or more embodiments, the superfascial button 104 is permanently attached to the screw 110. The screw 110 gets inserted into a threaded hole in the subfascial button 102. These three components make up what is referred to as the "wound closure device". The central insertion stem 108 screws into a threaded hole in the base of the subfascial button 102. The central insertion stem 108 is used by someone on the surgical team to guide the wound closure device into the wound. The hollow tube 106 slips over the central insertion stem 108 onto a connector on top of the superfascial button 104 can then be used to tighten the wound closure device onto the fascia around the wound. In one or more embodiments, the central insertion stem 108 is longer than the hollow tube 106, sufficiently longer so that the hollow tube 106 can be held by one person at the same time that another person (or the same person in the other hand) is holding the central insertion stem 108. Once the wound closure device is tightened, the central insertion stem 108 and hollow tube 106 can be removed.

Figure 2:
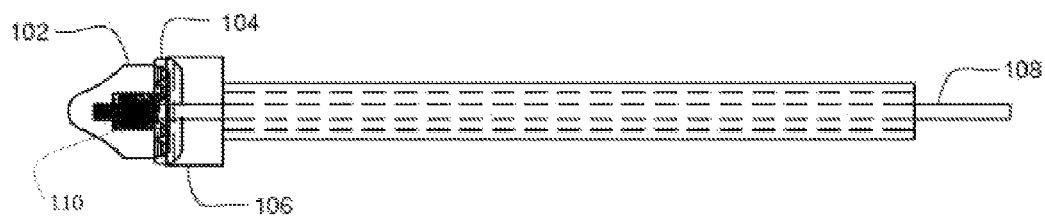
FIG. 2 shows a transparent view of the device for closing a wound in accordance with one embodiment of the present invention.

FIG. 2 shows a direct side-on hidden line view of an embodiment of the wound closure device, compression tool, and insertion tool. The subfascial button 102 is shown in position after compression against the superfascial button 104, with the hollow tube 108 and central insertion stem 108 still attached. The screw 110 attached to the superfascial button 104 is shown screwed into the subfascial button 102.

Figure 3:
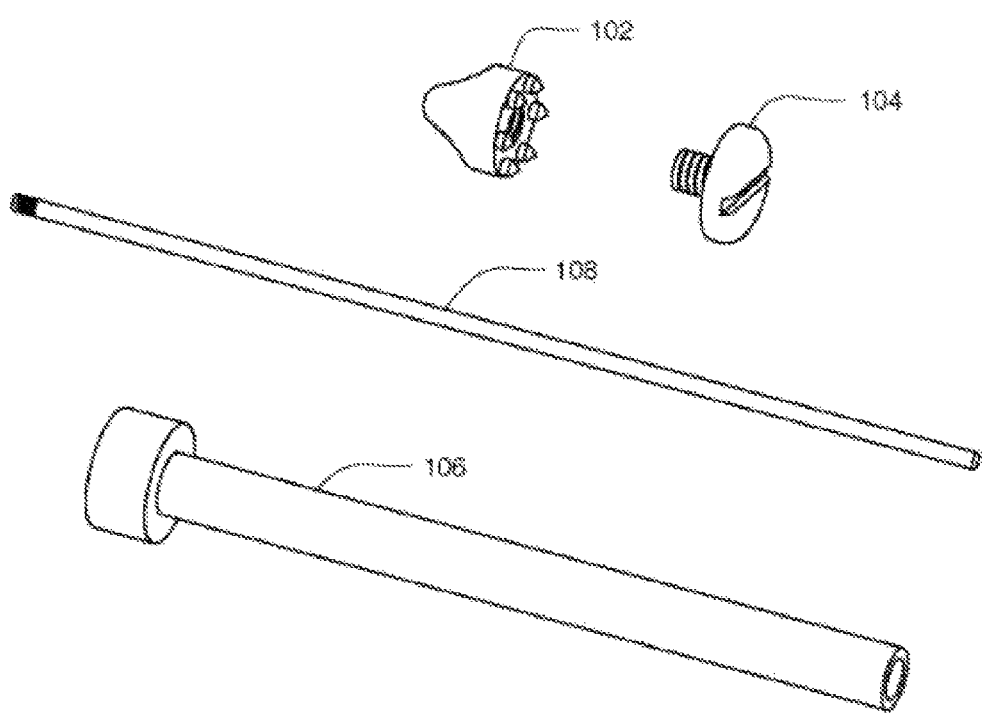
FIG. 3 shows a view of the disassembled parts in accordance with one or more embodiments of the present invention.

FIG. 3 shows a view of each of the parts disassembled. The subfascial button 102 will be attached to the superfascial button 104 via the screw 110. In one or more embodiments the screw is permanently attached to the superfascial button 104. The screw 110 and superfascial button 104 have a central hole large enough for the central insertion stem 108 to slide through so that it can be attached to the base of the subfascial button 102. Connecting the central insertion stem 108 to the base of the subfascial button 102 provides stability to the device during insertion. In one or more embodiments, the threads holding the central insertion stem 108 to the base of the subfascial button 102 are of an opposite handedness to the threads holding the screw 110 to the base of the subfascial button 102. This means that tightening one will not loosen the other.

Figure 4:
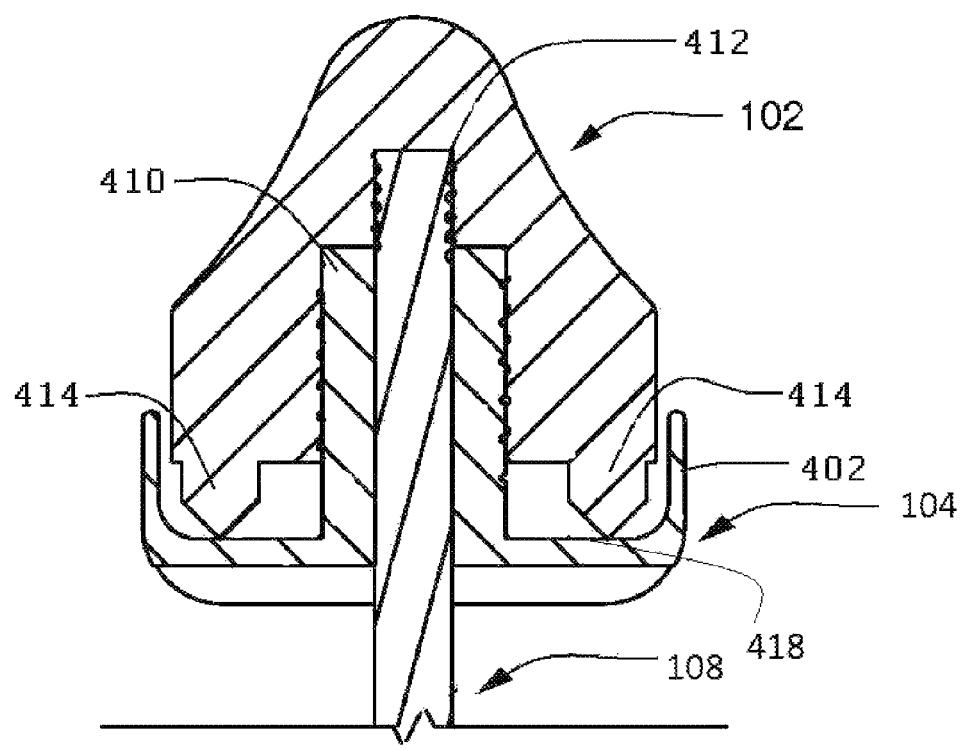
FIG. 4 shows a cross-section of an embodiment of the wound closure device.

FIG. 4 shows a cross-sectional view of the assembly. The face 420 of the subfascial button 102 has one or more protrusions 414 attached. The face 420 of the subfascial button is of a smaller diameter than the cupped 402 portion of the superfascial button 104, such that the protrusions 414 of the subfascial button 102 fit inside the cupped portion 402 of the superfascial button 104. The central insertion stem 108 fits into threads in the subfascial button 412 which extend from the threads in the subfascial button for the screw 410.

Subfascial Button

Figure 5:
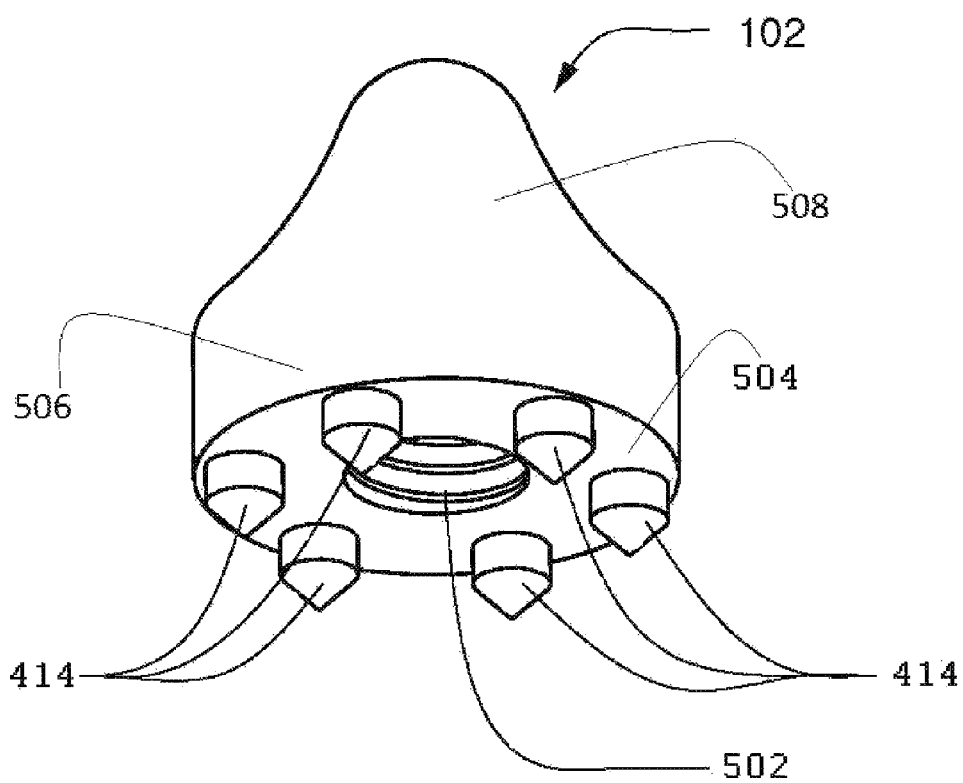
FIG. 5 shows a detailed bottom view of the subfascial button in accordance with one or more embodiments of the present invention.

FIG. 5 shows a view of the subfascial button as it is in one or more embodiments. The subfascial button 102 consists of a cone 508 and a base 506. The base 506 is of roughly constant diameter. In one or more embodiments, the cone 508 allows the wound closure device to push through the wound easier. The subfascial button has a hole with screw threads 502 substantially through the center of the face 504 extending through the base 506 and into the cone portion 508, such that the screw threads 502 are deep enough to stably connect the subfascial button 102 to the screw. The diameter of the subfascial button 102 at the end of the screw threads is such that neither reasonably sufficient torque on the screw to tighten it into the subfascial button 102 nor the act of pushing the subfascial button cone 508 through the fascia would cause the subfascial button 102 to crack. Not shown in the figure but clearly shown in other figures is a smaller hole deeper into the cone 412 than the hole for the screw 502. This hole is also substantially through the center, has threads of a handedness and diameter that it can connect with the central insertion stem 108.

In one or more embodiments, the subfascial button base 506 has a thin, flat profile of a few millimeters in thickness, is moderately rigid in structure and circular or elliptical in shape. This profile is desirable to lessen the likelihood of the patient's awareness of its presence or discomfort during the post-operative healing interval.

In one or more embodiments, a counter-rotational or frictional control feature can be added to the subfascial button face 504 such as small protrusions 414 of a conical shape to prevent the tendency to rotate during the process of tightening the superfascial button 104 onto the anterior surface of the fascia. In one or more embodiments, this frictional control feature is implemented where the face of the subfascial button 504 is textured with a patterned surface to offer frictional control such that, in use, the textured side is placed in direct contact with the fascia and associated layers of the abdominal wall, and covers the trocar defect. Its purpose is to align the edges of the linear defect and hold them in place to facilitate the healing process. In one or more embodiments, the texture is a non-smooth (unpolished) frictional control surface feature to assure that the subfascial button 102 remains in position and does not slide or shift laterally during the healing interval.

As deployed and implanted, the subfascial button 102 is located under the fascial defect and is a mating member of the wound closure device. Like the superfacial button 104, its goal is to close and securely align the trocar port defect in the fascia, and hold it in place for the intended healing interval. And, similarly, its purpose is fulfilled and completed at the end of the intended healing interval when the wound closure device should dissolve.

The Screw

The screw 110 is of such length so that it can be inserted into the subfascial button 102 and still has sufficient length to straddle the fascia. In one or more embodiments, it must also be of large enough diameter to enable the central insertion stem 108 to be inserted through the screw into the finer threads of the subfascial button. In one or more embodiments, the length of the screw 110 can be made at varying lengths to enable use for patients with differing tissue thicknesses and minimize the exposure of the screw 110. In one or more embodiments, the screw 110 is permanently attached to the bottom of the superfascial button 104. In other embodiments, the screw 110 is independent of the subfascial button and superfascial button 104, and so the length of the screw 110 must be taken into account to minimize the length of the screw 110 present beyond the superfascial button 104.

In one or more embodiments, the diameter of the screw 110 may be made at varying widths to support the closure of different diameter wounds. In one or more embodiment, the screw 110 has a hole through its center which accepts the central insertion stem 108. In one or more embodiments, where the screw 110 is not permanently attached to the superfascial button 104, to prevent loosening, the threads between the screw 110, superfascial button 104 and subfascial button 102 are a different hand-sense (i.e. right-handed vs. left-handed) than the threads between the subfascial button 102 and central insertion stem 108.

In one or more embodiments, the screw 110 can be permanently connected to either the subfascial button 102.

In one or more embodiments, the screw 110 may be replaced by a locking or clasping mechanism. This locking or clasping mechanism can be configured with frictional features or ratcheting and interlocking protrusions to secure the subfascial button base 420 and superfascial button base 418 components together, and hold them with the desired degree of tension across the fascia and associated layers.

Superfascial Button

Figure 6:
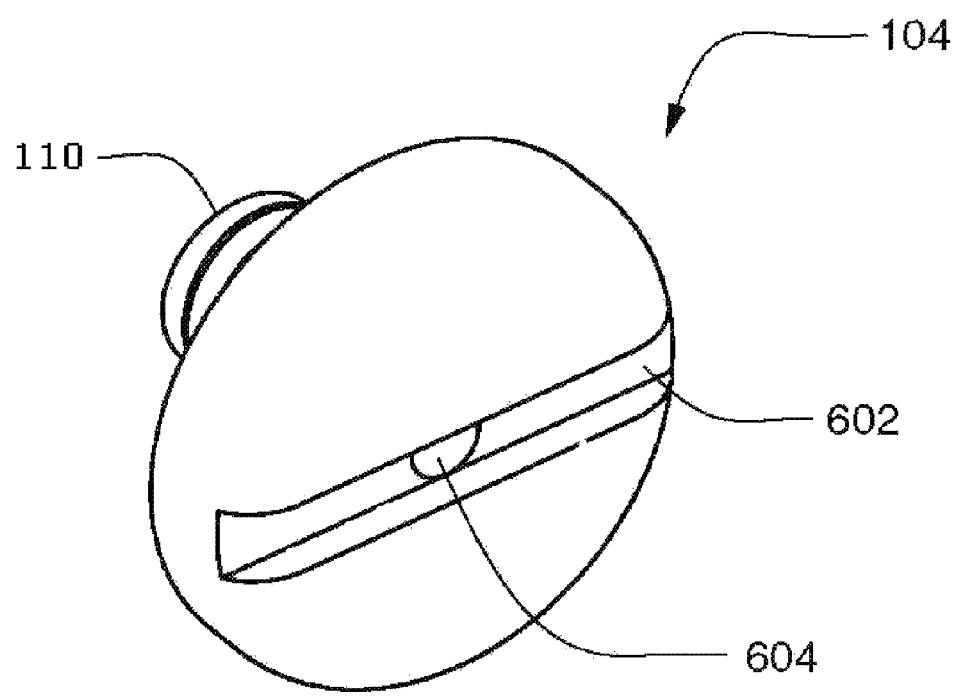
FIG. 6 shows a detailed top view of the superfascial button along with its attached screw in accordance with one or more embodiments of the present invention.

As shown in FIG. 6, the superfascial button 104 consists of a base 606 and a connector 602, the base 606 being closer to the fascia. The superfascial button 104 has a hole through the center 604 which allows the central insertion stem 108 to be slipped through it. In one or more embodiments, the connector 602 consists of one or more grooves that are deep enough so that a compression tool with protrusions could be inserted into the grooves. The compression tool would have enough contact between the protrusions and the grooves such that torque can be applied by the tool to tighten the superfascial button 104 onto the subfascial button 102.

Figure 7:
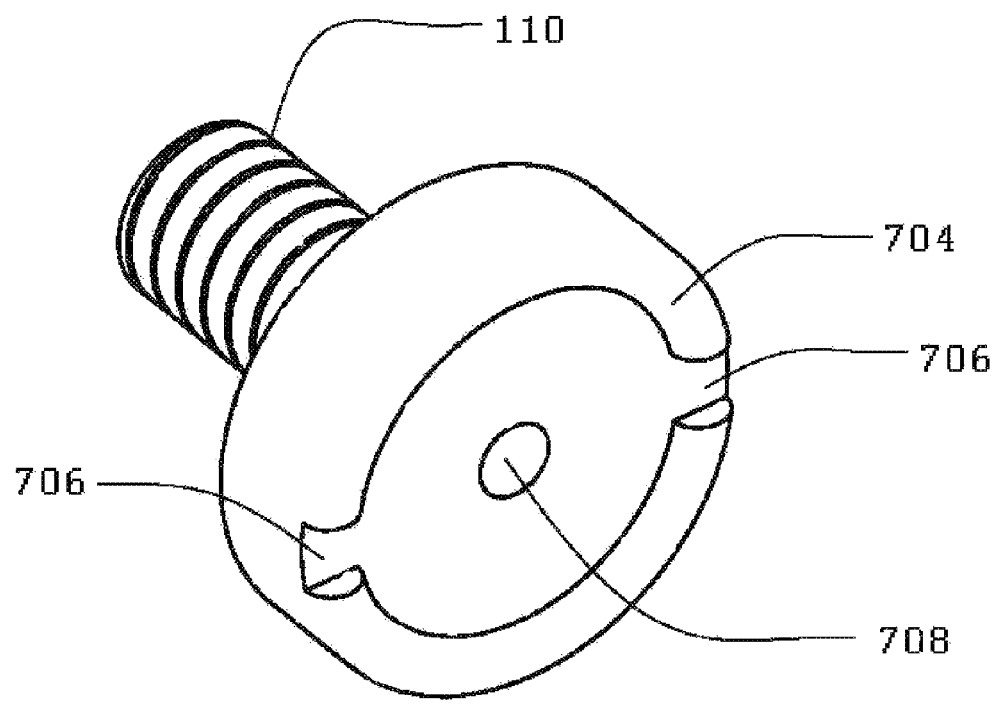
FIG. 7 shows a view of the top of the superfascial button in accordance with one or more embodiments of the invention.

As shown in FIG. 7, in one or more embodiments, the connector may be embodied as a raised ring 704 with two or more notches 706 in the ring. These notches 1006 are in a pattern that matches the pattern of protrusions attached to the end of an embodiment of a compression tool. The notches 706 are of enough width to accommodate the protrusions. As with other embodiments, this embodiment would also have a screw attached 702 and a hole 708 to allow the central insertion stem 108 to slip through it.

Figure 8:
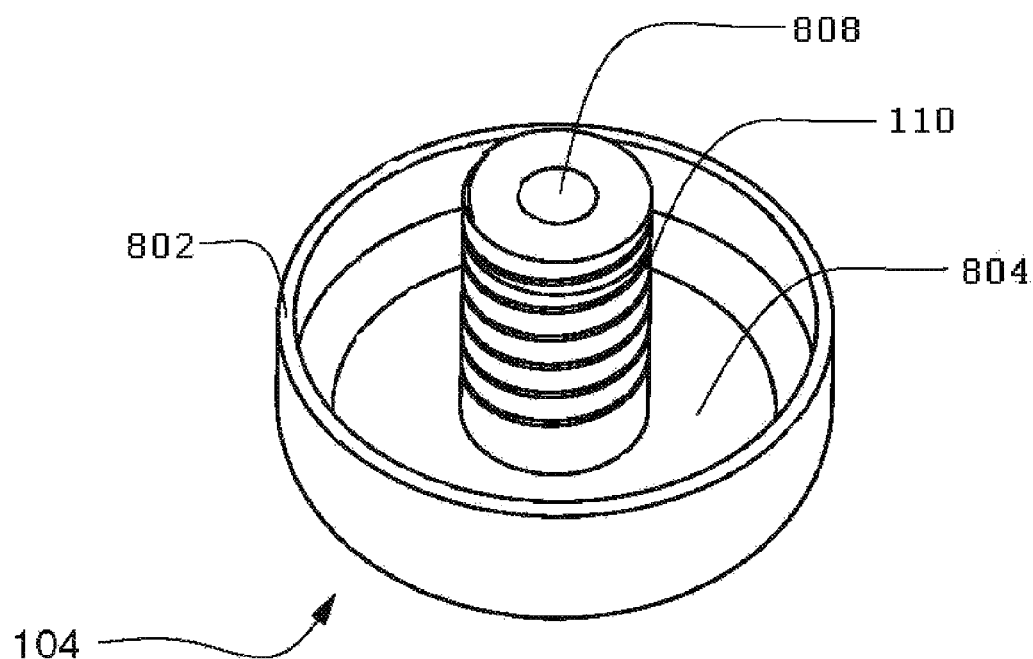
FIG. 8 shows a view of the bottom of the superfascial button and screw assembly for one or more embodiments of the current invention.

An embodiment of the superfascial button 104 is shown in FIG. 8. In one or more embodiments, the superfascial button base 804 has a thin, flat profile of a few millimeters in thickness, is moderately rigid in structure and circular or elliptical in shape. This profile is desirable to lessen the likelihood of the patient's awareness of its presence or discomfort during the post-operative healing interval. In one or more embodiments, the base would have sides which curve upward at the edges 802. The sides should be high enough above the flat profile so that fascia and associated layers are engaged between the inner wall of the side and the edge of the subfascial button. By doing so, the sides encourage the device to remain at the location of wound, further assuring the anatomical alignment of the wound edges, and countering the tendency of the fascia and associated layers to pull away.

In one or more embodiments, the screw 110 is permanently attached to the base 806. There is a hole in the screw 808 that is aligned with the hole through the superfascial button 604. The hole is of such size and shape to allow the central insertion stem 108 to slip through it.

In one or more embodiments, the superfascial button base 606 has a thin, flat profile of a few millimeters in thickness, is moderately rigid in structure and circular or elliptical in shape. This profile is desirable to lessen the likelihood of the patient's awareness of its presence or discomfort during the post-operative healing interval.

General Composition of the Wound Closure Device

Materials specified for the wound closure device are specific for its intended application and use. The scope of materials that will satisfy the requirements of this application is unusually narrow. This is a direct consequence of the specificity and functional demands characteristic of the intended surgical application.

The intention for the wound closure device is to close and secure the trocar port defect in the fascia. This requires a known and finite healing interval of some three to five months. Its purpose fulfilled at the end of this period, making continued presence of the closure device a potential liability. To prevent it from becoming a source for irritation once the healing process is completed, the implanted closure device should be removed. Consequently, to avoid the need for a second surgical intervention to remove the device, Maurus and Kaeding (Maurus, P. B. and Kaeding, C. C., "Bioabsorbable Implant Material Review", *Oper. Tech. Sports Med* 12, 158-160, 2004) found it was a primary requirement for the wound closure device is that it is biodegradable. This means that the materials will degrade or disintegrate, being absorbed in the surrounding tissue in the environment of the human body, after a definite, predictable and desired period of time. One advantage of such materials over non-degradable or essentially stable materials is that after the interval for which they are applied (i.e. healing time) has elapsed, they are no longer a contributing asset and do not need subsequent surgical intervention for removal, as would be required for materials more stable and permanent. This is most significant as it minimizes risks associated with repeat surgeries and the additional trauma associated with these procedures.

A disadvantage of these types of materials is that their biodegradable characteristic makes them susceptible to degradation under normal ambient conditions. There is usually sufficient moisture or humidity in the atmosphere to initiate their degradation even upon relatively brief exposure. This means that precautions must be taken throughout their processing and fabrication into useful forms, and in their storage and handling, to avoid moisture absorption. This is not a serious limitation as many materials require handling in controlled atmosphere chambers and sealed packaging; but it is essential that such precautions are observed. Middleton and Tipton (Middleton, J. and Tipton A. "Synthetic Biodegradable Polymers As Medical Devices" *Medical Plastics and Biomaterials Magazine*, March 1998) found that this characteristic also dictates that their sterilization before surgical use cannot be done using autoclaves, but alternative approaches must be employed (e.g. exposure to atmospheres of ethylene oxide or gamma radiation with cobalt 60).

While biodegradability is an essential material characteristic for the wound closure device, the intended application is such that a further requirement is that the material is formulated and manufactured with sufficient compositional and process control to provide a precisely predictable and reliable degree of biodegradability. This means a typical biodegradation interval of three to five months, corresponding to the healing interval for the trocar defect in the fascia layer.

In these materials, simple chemical hydrolysis of the hydrolytically unstable backbone of the polymer is the prevailing mechanism for its degradation. As discussed in Middleton and Tipton (Middleton, J. and Tipton A referenced previously), this type of degradation when the rate at which water penetrates the material exceeds that at which the polymer is converted into water-soluble materials is known as bulk erosion.

Biodegradable polymers may be either natural or synthetic. In general, synthetic polymers offer more advantages than natural materials in that their compositions can be more readily finely-tuned to provide a wider range of properties and better lot-to-lot uniformity and, accordingly, offer more general reliability and predictability and are the preferred source.

Synthetic absorbable materials have been fabricated primarily from three polymers: polyglycolic acid (PGA), polylactic acid (PLA) and polydioxanone (PDS). These are alpha polyesters or poly (alpha-hydroxy) acids. The dominant ones are PLA and PGA and have been studied for several decades. Gilding and Reed (Gilding, D. K and Reed A. M., "Biodegradable Polymers for Use in Surgery" *Polymer* 20, 1459-1464) discussed how each of these materials has distinctive, unique properties. One of the key advantages of these polymers is that they facilitate the growth of blood vessels and cells in the polymer matrix as it degrades, so that the polymer is slowly replaced by living tissue as the polymer degrades ("Plastic That Comes Alive: Biodegradable plastic scaffolds support living cells in three dimensional matrices so they can grow together into tissues and even whole organs" by Cat Faber *Strange Horizons* http://www.strangehorizons.com/2001/20010305/plastic.shtml)

In recent years, researchers have found it desirable for obtaining specific desirable properties to prepare blends of these two dominant types, resulting in a highly useful form, or co-polymer, designated as PLGA or poly (lactic-co-glycolic acid). Asete and Sabilov (Asete, C. E. and Sabilov C. M., "Synthesis and Characterization of PLGA Nanoparticles", *Journal of Biomaterials Science—Polymer Edition* 17(3) 247-289 (2006)) discuss how this form is currently used in a host of FDA-approved therapeutic devices owing to its biodegradability and biocompatibility.

In one or more embodiments, the biodegradable wound closure device may be made of biodegradable material of different stability (i.e. half-life). While it is important for the material that is in direct contact with the fascia or lending support to that (the subfascial button base 506, screw 110, and superfascial button base 606) needs to stay in place for a few months, while the rest of the implantable structure can degrade significantly in a matter of weeks without affecting the performance of the payload. In one or more embodiments, the screw 110 would degrade sooner than the subfascial button base 506 and superfascial button base 606, so that the ends of the defect are allowed to grow together while protecting the surface of the defect.

Material for the Subfascial Button

Owing to its necessarily and virtually inaccessible location beneath the fascia and peritoneum and its need to be placed and positioned correctly and precisely in proper alignment with the superfascial button base 606 located on the other side, the material used for the subfascial button base 506 must be even more specialized than the superfascial button base 606. That is, besides the same requirement for biodegradability and biocompatibility, the additional need for its placement and positioning in a virtually inaccessible and invisible location imposes much more stringent specifications and limitations upon the grade of polymer used for this component.

In one or more embodiments, the subfascial button 102 is made from shape memory biodegradable polymer, such that the cross-section of its insertion is small, but over time it expands against the fascia. In one embodiment, it would be inserted in a teardrop shape, and once in place expand into a flattened disc-like shape.

Although various pre-insertion bending and folding manipulative procedures might be conceived and envisioned for controlling the profile of the subfascial button base 506 to enable it to be inserted into and through the subcutaneous tissue and fascial defect and then, somehow, unfolded and flattened, and deployed into its desired position correctly aligned with the superfascial button 104; such requirements are considered essentially unreliable, excessively time-consuming and of seriously doubtful feasibility for a practical and increasingly common surgical procedure. For these reasons, in one or more embodiments of the invention, the material contemplated for the subfascial button base 506 is a co-polymer having the desired biodegradability characteristics for the application, but also one that possesses a shape-memory property. Shape memory polymers are discussed in Lendlein and Kelch (Lendlein, A. and Kelch, J. "Shape-Memory Polymers" *Angewandte Chem. Int. Ed.*, 41, 2034-2057 (2002)) and described further in Kawai and Matsuda (U.S. Pat. No. 4,950,258, issued Aug. 21, 1990).

Polymer systems with shape-memory properties have an attractive and broad application potential in minimally invasive (e.g. laparoscopic) surgery, the field of interest for this invention. Absorbable implants of the material can be inserted into the human body in a compressed or deformed (temporary) shape through a small incision (as the trocar fascial defect of this disclosure). After being placed into the desired position, (Kawai and Matsuda (U.S. Pat. No. 4,950,258, issued Aug. 21, 1990) described how shape memory polymers can be reverted back to their desired final functional shape upon warming to body temperature.

During the appropriate healing interval, the implant is degraded and absorbed, making subsequent surgery to remove the implant unnecessary. These shape-memory materials may be suitably modified to achieve the precisely desired behavior for specific applications.

For biomedical applications such as the wound closure device, a thermal transition of the shape of the shape-memory material in a fairly narrow temperature range between room (ambient) and body temperature is desired. Such materials have been developed and are available for application in the present contemplated invention. Nevertheless, because of the demanding nature of this application and the need for rigidly narrow operating temperature limits, as well as assurance of adequate mechanical properties, it is expected and probably unavoidably necessary that some co-polymer development will be required to achieve an optimal balance of properties for this very specific application.

In use, and having an implantable subfascial button 102 of the desired geometry of optimal material, the circular or elliptically shaped disc would be deformed such that its deformed profile would be readily insertable into and through the subcutaneous tissue layer and trocar fascial defect. This maneuver would desirably take place within a brief time interval to assure that the polymeric material did not reach its shape-memory transition temperature (i.e. body temperature) before being positioned into its required and desired location behind or under the fascial defect.

Material for the Superfascial Button

Depending upon the ratio of lactide-to-glycolide used for polymerization, different forms or grades of PLGA are obtainable. These are usually identified according to the monomers' ratio and are so designated in the literature and suppliers' brochures. PLGA has been successful as a biodegradable polymer for medical applications because it undergoes hydrolysis in the body to produce the original monomers, lactic acid and glycolic acid.

The two monomers associated with PLGA, lactide and glycolide, under normal physiological conditions, are byproducts of various metabolic pathways in the human body. Since the body effectively deals with these two monomers, there is minimal system toxicity associated with use of this co-polymer. A notable feature of PLGA is that it is possible to tailor the polymer degradation interval by adjusting the ratio of monomers. In light of the versatility of the PLGA co-polymer and its record of successful use in a wide range of bio-absorbable applications, it is the specified material for the superfascial button base 606.

Insertion Tool

In one or more embodiments, the insertion and the minimal positioning expected to be required would be accommodated with an attached positioning stem fastened to the subfascial button 102. The insertion tool consists of an insertion mechanism to place the wound closure device into position at the fascia defect. In one or more embodiments, the insertion mechanism is a central insertion stem 108, as described below.

Central Insertion Stem

Figure 9:
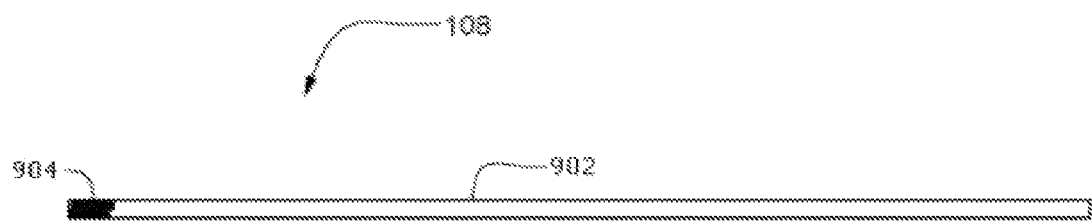
FIG. 9 shows a detailed view of the central insertion stem in accordance with one or more embodiments of the present invention.

The central insertion stem enables the wound closure device to be inserted through the trocar tunnel (subcutaneous tissue layer) and fascial defect and placed below the fascia. As shown in FIG. 9, the central insertion stem 108 is a solid piece of cylindrical material which is threaded at the lower end. These threads 904 are of sufficient length to attach to the biodegradable wound closure device into the screw to hold the biodegradable wound closure device steady throughout an insertion procedure. The stem handle 902 must be of significant length to be grasped while simultaneously grasping the outer tube body. In one or more embodiments, the diameter of the central insertion stem 108 used in a particular procedure may vary to support different wound sizes.

The central insertion stem 108 would extend up and out in a forward anterior direction through the fascia defect and be manually manipulatable by the surgeon. At this point, with the subfascial button in its proper position under the fascia defect, it can be brought up against the peritoneum and underside of the fascia by the surgeon simply exerting an upward (outward) manual force upon the central insertion stem.

In one or more embodiments, a frictional or ratcheting holding feature is provided between a hole in the superfascial button and the lower surface of the central insertion stem whereby the superfascial button becomes secured to the central insertion stem, allowing the subfascial button base 506 and superfascial button base 606 to sandwich the fascia and associated layers between them. This feature is designed to allow the desired degree of compressive force to be maintained without further application of continual external manual pressure. At this point in the closure device implant procedure the closure device is self-sustaining, independent of the need for external force and in its desired position.

Outer Tube

Figure 10:
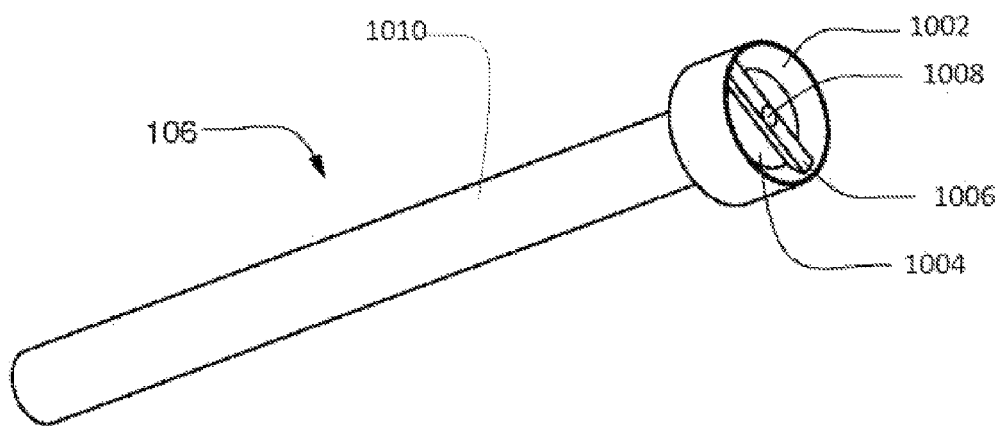
FIG. 10 shows a detailed view of the hollow tube component in accordance with one or more embodiments of the present invention.

As shown in FIG. 10, the outer tube 106 is a hollow tube that fits over the central insertion stem 108 at one end and into the connector of the superfascial button 602 at the other. The outer tube 106 has a body 1010 that is of significant length to enable one to grasp it comfortably from outside the body, and one or more protrusions 1006 which enable the outer tube 106 to detachably connect to the connector 602. The inner diameter of the outer tube 106 should be significantly greater than the diameter of the central insertion stem 108. In one or more embodiments, the outer diameter of the outer tube 106 must be smaller than the diameter of the superfascial button 104 to allow the outer tube 106 to sit on top of the superfascial button 104. In other embodiments, the outer tube 106 may be wider than the superfascial button 104 such that the protrusions 1006 on the bottom of the outer tube can be inserted into the grooves 602 on the superfascial button 104.

In one or more embodiments, the face of the outer tube 1004 is surrounded by a curved edge 1002 in such a way so that it substantially covers the head of the superfascial button, improving the stability of the connection between the outer tube and superfascial button.

Once the wound closure device has been put into place by the central insertion stem 108, the outer tube 106 would be introduced to allow the surgeon to assure mutual seating of both the subfascial button 102 and superfascial button 104 tightly against either side of the fascia. This would simply require application of an upward manual force to the central insertion stem (attached to the subfascial button) and simultaneously-applied downward pressure to the hollow tube 106 contacting the superfascial button 104. Such opposing manual forces would readily bring the superfascial button 104 and subfascial button 102 together with the fascia sandwiched in between. In one or more embodiments, this downward force on the hollow tube 106 would also require a torque force to turn the superfascial button 104 so that it moves closer to the subfascial button.

The wound closure device only comes into play toward the end of the surgical event, after the surgical procedure has essentially been completed. At this stage, the intent is to close the trocar port to prevent any subsequent risk of herniation at the defect sites, a risk with present suturing closure methods. Accordingly, since the trocar will have already been removed along with the videoscope, and the abdominal cavity deflated, visibility and maneuverability within the abdominal cavity are necessarily severely restricted. This is in contrast to the significantly more accessible and visible situation at this location during the surgical procedure itself.

Material of the Central Insertion Stem

In one or more embodiments, the central insertion stem 108 is made of material that is non-reactive but not itself biodegradable. The central insertion stem 108 can be discarded or reused, and may be made in varying lengths to enable surgeons in different situations dealing with patients of different sizes to be able to control the placement of the biodegradable wound closure device.

In one or more embodiments, the central insertion stem 108 is fabricated of two polymers of differing grades—a short-term degradation material at the protruding end, and a longer-term material at the location of the holding mechanism. Such a dual-material component might be readily assembled using a mechanical or other joint type at the desired location along its length, where the two polymer grades intersect. Upon completion of the surgical procedure and implanting of the wound closure device, the protruding central insertion stem 108 can be cut off below the anterior surface of the subcutaneous layer but above the juncture of the two grades of polymer. With a short-term biodegradable material for the anterior portion of the central insertion stem 108—well beyond the superfascial button 104 and its securing frictional or ratcheting feature—the potential problem with stem removal is eliminated. To avoid a possible mix-up during fabrication and assembly of such a dual-material central insertion stem the different grades of polymer could be tinted different colors.

DESCRIPTION OF USE OF ONE OR MORE EMBODIMENTS OF THE INVENTION

One or more embodiments of the use of this invention are described herein.

Connect the subfascial button 102 to the assembly consisting of the screw 306 and superfascial button 104. In one or more embodiments, the superfascial button 104 could be a separate component which needs to be connected to the screw 306. The central insertion stem 108 can then be connected to the biodegradable wound closure device by threading it onto the screw 110. In one or more embodiments, the superfascial button 104 can be inserted over the central insertion stem 108 prior to attempting to implant the wound closure device. In other embodiments, the superfascial button 104 can be inserted after the subfascial button 102 is implanted. In other embodiments, the superfascial button 104 is permanently attached to the screw 110, such that the superfascial button-screw assembly is threaded into the subfascial button 102, and the central insertion stem 108 is threaded into a threaded hole in the subfascial button 412.

Using the central insertion stem 108, guide the biodegradable wound closure device to the wound site and press it through the site. Then pull back on the central insertion stem 108 to cinch it in place. In one or more embodiments, if not already done place the superfascial button 104 on the central insertion stem 108, connector-side up and allow it to slide into position at the top of the subfascial button 104.

Figure 11:
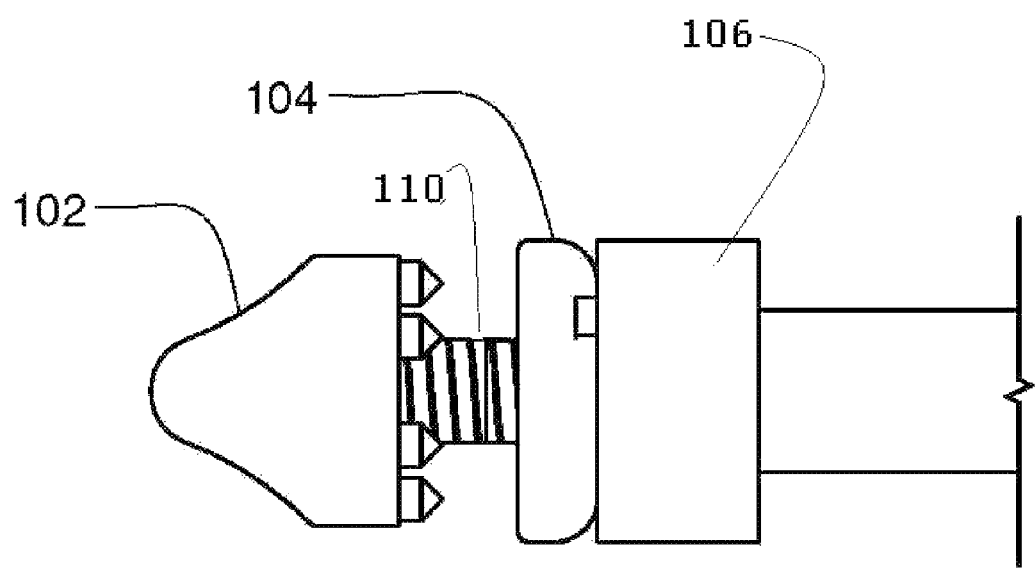
FIG. 11 shows a view of the device in accordance with one or more embodiments of the current invention.

Once the biodegradable wound closure device is in place, place the outer tube 106 over the central insertion stem 108 by sliding the outer tube over the central insertion stem 108 through the hole in the outer tube 408 and slide the outer tube 106 into place over the superfascial button connector 602. FIG. 11 shows what the configuration would look like in one or more embodiments of the present invention.

Rotate the outer tube 106 until the outer tube protrusions 1006 line up with the superfascial button connector 602. The outer tube 106 should drop slightly so that the protrusions 1006 are inside the superfascial button connector 602.

Figure 12:
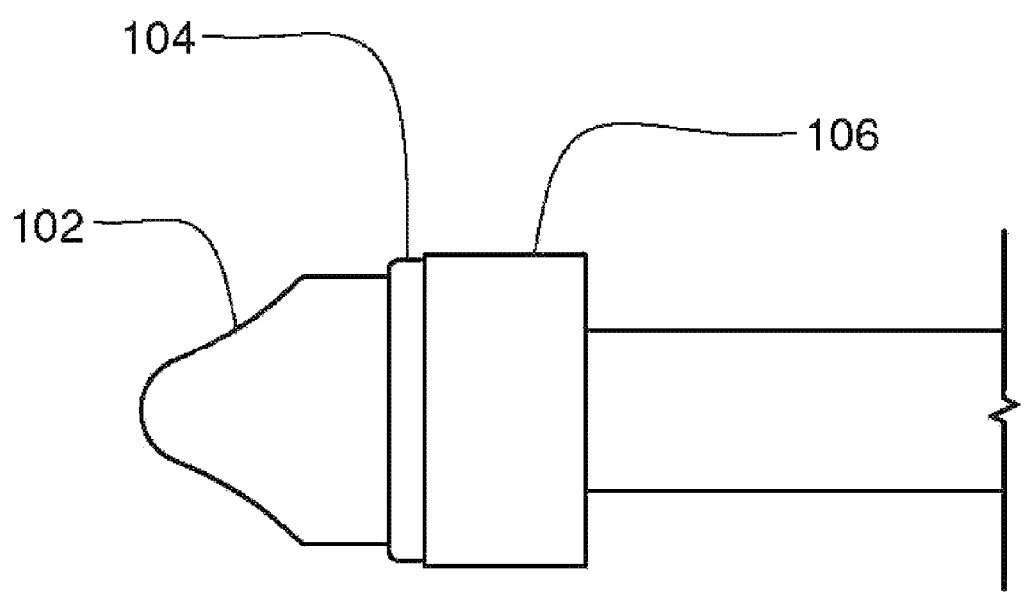
FIG. 12 shows a view of an embodiment of the wound closure device when it is being compressed into the wound.

Once the outer tube 106 is in place, it can be used to compress the biodegradable wound device against the fascia and associated abdominal layers. While grasping the central insertion stem 108 with one hand. Rotate the outer tube 106 in the direction appropriate to the threads of the screw 110, until it feels tight. In one or more embodiments, this direction would be the opposite sense of the threads on the central insertion stem 904 to prevent it from slipping out. FIG. 12 shows the resulting configuration where the biodegradable wound device has been compressed.

Figure 13:
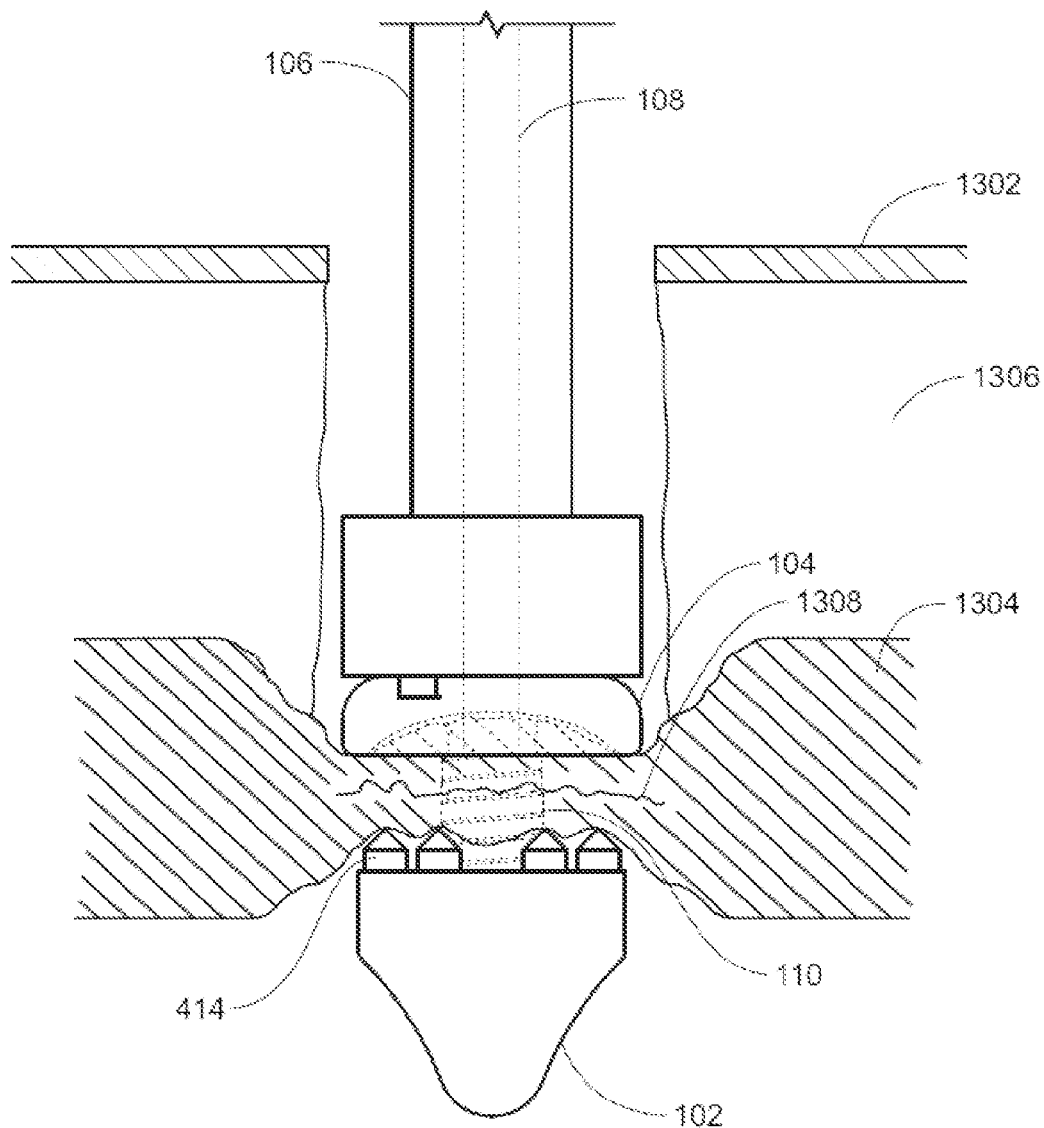
FIG. 13 shows a view of an embodiment of the device being inserted through the tunnel.

FIG. 13 shows an embodiment of the invention in place. As stated previously, the laparoscopic trocar is removed, leaving a residual defect in the fascia-peritoneal layer 1306 under the skin 1302 which goes through the skin 1302 and intermediate tissue layers above the fascia 1306 and into the wound 1308, after the laparoscopy tunnel and surgical tools have been removed. The ability for the surgeon to see into the wound is impaired because there is nothing holding the sides of the wound up. The surgeon would hold the central insertion stem 108 to keep the subfascial button 102 in place while applying a rotational force to the outer tube 106 over the screw 110 to move the superfascial button 104 toward the subfascial button 102. This results in compressing the fascia between 1304 it.

Figure 14:
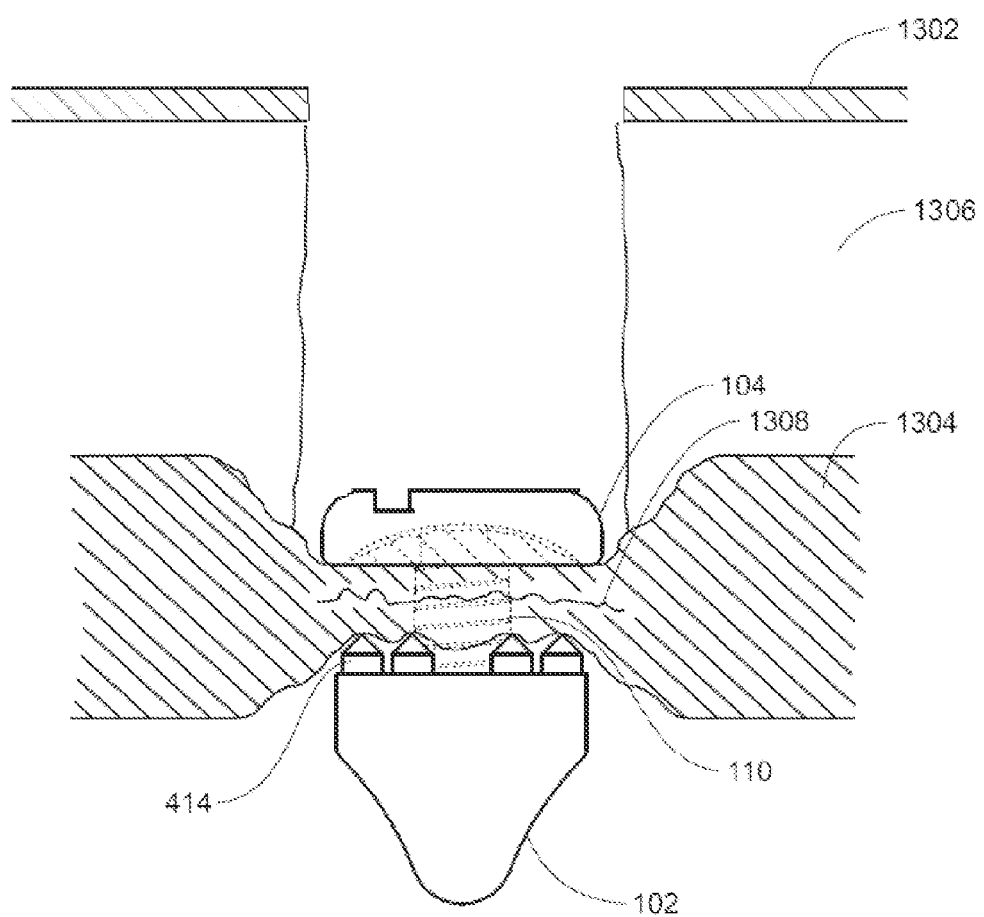
FIG. 14 shows a view of an embodiment of the device in place.

FIG. 14 shows an embodiment of the invention after the central insertion stem 108 and outer tube 106 have been removed. The fascia 1304 is compressed and pushed into the area under the superfascial button 104 by the protrusions 414 on the subfascial button 102. The combination of the compression and pushing mechanism acts to keep the device in place after the insertion process is complete.

Figure 15:
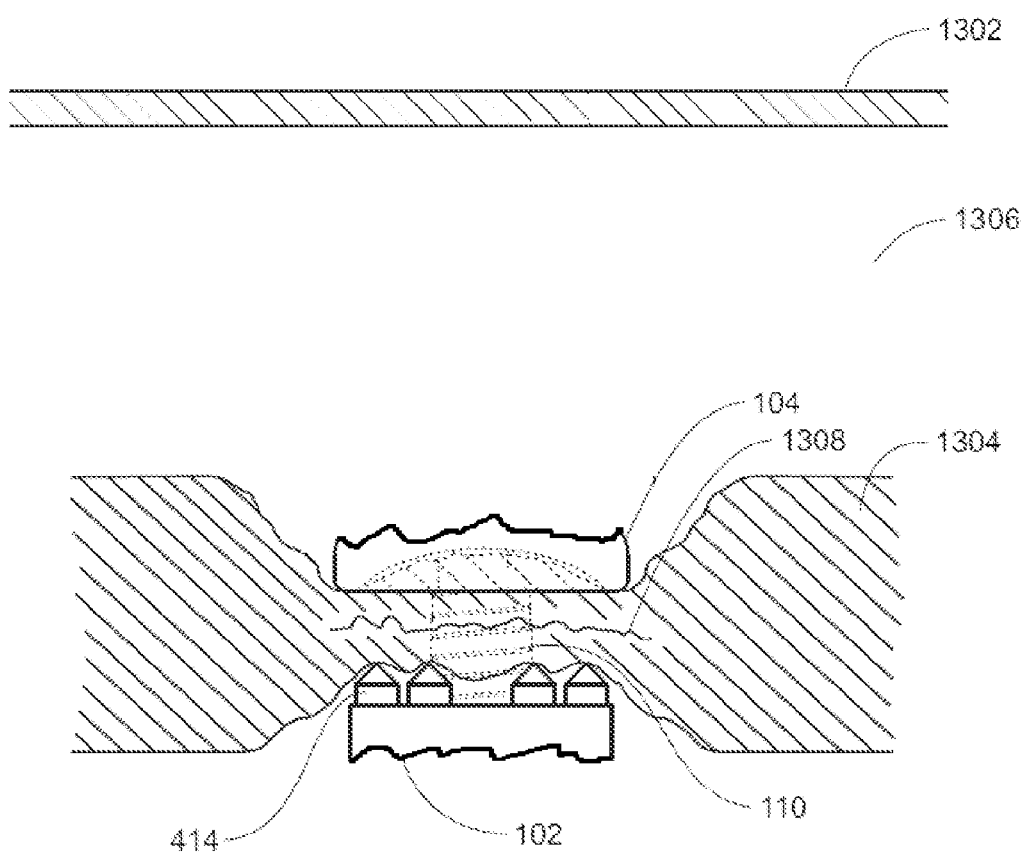
FIG. 15 shows a view of an embodiment of the device during the healing process.

FIG. 15 shows an embodiment of the invention during the healing process. The skin 1302 and fascia-peritoneal layer 1306 have healed over the area of the tunnel and the wound 1308 is healing. The material of the screw 110, subfascial button 102, and superfascial button 104 are still on the wound 1308 because of the initial compression and pushing of the tissue, but are degrading. By the time they degrade to the point where they no longer provide any engagement with the fascia tissue 1304, the wound 1308 will have healed sufficiently to complete the process.

Once the wound closure device has been compressed against the fascia as shown in FIG. 13, the outer tube 106 can be removed. FIG. 14 shows an embodiment of the wound closure device against the fascia wound 1308 with the central stem removed. The wound closure device is left in place by unscrewing the central insertion stem 108 from the subfascial button threads 412. The wound can be closed at the epidermal layers. As shown in FIG. 15, the fascia wound 1308 will heal and the biodegradable wound closure device will dissolve over time. In one or more embodiments, the biodegradable wound closure device will be constructed of biodegradable polymers of various expected degrading times, such that the parts of the wound closure device which are not required to hold the wound in place will dissolve faster than the parts that are required to hold the wound in place.

What is claimed is:

1. A biodegradable implantable device for maintaining the alignment of the edges of a trocar defect, the trocar defect having a defect diameter, the fascia and associated layers around the trocar defect having a thickness, the device comprising:
    a first biodegradable base having a first base diameter substantially equal to the defect diameter, the first biodegradable base having:
        a first surface, the first surface capable of substantially contacting the posterior wall of the trocar defect,
        a first threaded hole substantially through the center extending inward from the first surface but not all the way through the first biodegradable base, and
        a second threaded hole extending inward from the first threaded hole but not all the way through the first biodegradable base;
    a second biodegradable base having a second base diameter, the second biodegradable base further comprising:
        a first surface with a protruding ring along its outer edge, where the inner diameter of the protruding ring is greater than the first base diameter, such that the first surface of the first biodegradable base fits inside the inner walls of the protruding ring of the second biodegradable base with sufficient gap to allow reliable engagement of the fascia and associated layers with the device;
        a second surface with a plurality of slots of such depth and width to allow engagement with a plurality of mating protrusions on an external tool, and
        an unthreaded hole substantially through the center of the first surface and the second surface, the diameter of the hole substantially equal to the diameter of the second threaded hole in the first biodegradable base, configured to allow a device with the diameter and threading to mate with the second threaded hole in the first biodegradable base to pass through unobstructed; and
    a biodegradable connector for connecting the first surface of the first biodegradable base with the first surface of the second biodegradable base, the biodegradable connector defined to compress the first biodegradable base against the second biodegradable base using an external force,
        wherein the length of the connector is sufficient to connect to the first biodegradable base and the second biodegradable base while allowing enough space to maintain a predefined gap substantially equal to the tissue thickness between the first surface of the biodegradable base and the first surface of the second biodegradable base, and the biodegradable connector having an unthreaded hole substantially through the middle of the same size and alignment as the unthreaded hole in the second biodegradable base, allowing a device with the diameter and threading to mate with the second threaded hole in the first biodegradable base to pass through unobstructed,
    wherein the biodegradable connector threads into the first threaded hole of the first biodegradable base, and
    the diameter of the first threaded hole of the first biodegradable base is greater than the diameter of the second threaded hole of the first biodegradable base.

2. The biodegradable implantable device in claim 1, wherein the biodegradable connector, first biodegradable base, and second biodegradable base are made from biodegradable polymers of differing degradation rates so that the biodegradable connector degrades faster than the first and second biodegradable bases.

3. The biodegradable implantable device in claim 1, wherein the first biodegradable base is made of a shape-memory biodegradable polymer, wherein it can be inserted with a smaller cross-section than it assumes after a short exposure to body temperature, at which point it covers a larger cross-section of the trocar defect.

4. The biodegradable implantable device in claim 3, wherein the shape-memory biodegradable polymer is shaped like a teardrop, and expands to a disc-like shape against the trocar defect after exposure to body temperature.

5. The biodegradable implantable device in claim 1, wherein the biodegradable connector comprises a screw, wherein the screw is attached to the first biodegradable base and threads into the second biodegradable base.

6. The biodegradable implantable device in claim 5, wherein the first threaded hole threads of the first biodegradable base are the opposite handedness of the second threaded hole of the first biodegradable base.

7. The biodegradable implantable device in claim 6, further comprising a biodegradable cone, the biodegradable cone connected to the second surface of the first biodegradable base.

8. The biodegradable device in claim 7, wherein the first surface of the first biodegradable base further comprises a frictional control mechanism to prevent the fascia and associated layers contacting the first surface from sliding or shifting laterally while in contact with the first surface.

9. The device in claim 8, wherein the biodegradable cone, first biodegradable base, and second biodegradable base and biodegradable connector are made from biodegradable polymers of differing degradation rates so that the biodegradable connector and biodegradable cone degrade faster than the first and second biodegradable bases.

10. The biodegradable implantable device in claim 1, wherein the biodegradable connector comprises a screw, wherein the screw is attached to the second biodegradable base and threads into the first biodegradable base.

11. The biodegradable device in claim 1, wherein the first surface of the first biodegradable base further comprises a frictional control mechanism to prevent the fascia and associated layers contacting the first surface from sliding or shifting laterally while in contact with the first surface.

12. The biodegradable device in claim 11, where the frictional control mechanism on the first surface of the first biodegradable base could be one of:
   small conical protrusions distributed radially on the first surface of the first biodegradable base, the vertex of the protrusions facing away from the first surface, texturing the first surface, or
   leaving the first surface unpolished.

13. The device in claim 11, wherein the first biodegradable base, and second biodegradable base and biodegradable connector are made from biodegradable polymers of differing degradation rates so that the parts of the components used to implant the biodegradable implantable device degrade faster than the parts of the components used to compress the wound.

14. The device in claim 11, wherein the second surface of the second biodegradable base further comprises ridges.

15. The device in claim 11, wherein the second surface of the second biodegradable base further comprises a raised ring, such that the raised ring has notches to enable insertion of a tool to apply a torque to the second biodegradable base.

16. A biodegradable implantable device for maintaining the alignment of the edges of a trocar defect, the trocar defect having a defect diameter, the fascia and associated layers around the trocar defect having a thickness, the device comprising:
   a first biodegradable base having a first base diameter substantially equal to the defect diameter, the first biodegradable base having:
      a first surface, the first surface capable of substantially contacting the posterior wall of the trocar defect,
      a first hole substantially through the center extending inward from the first surface but not all the way through the first biodegradable base, and
      a second threaded hole extending inward from the first hole but not all the way through the first biodegradable base;
   a second biodegradable base having a second base diameter, the second biodegradable base further comprising:
      a first surface with a protruding ring along its outer edge, where the inner diameter of the protruding ring is greater than the first base diameter, such that the first surface of the first biodegradable base fits inside the inner walls of the protruding ring of the second biodegradable base with sufficient gap to allow reliable engagement of the fascia and associated layers with the device;
      a second surface with a plurality of slots of such depth and width to allow engagement with a plurality of mating protrusions on an external tool, and an unthreaded hole substantially through the center of the first surface and the second surface, the diameter of the hole substantially equal to the diameter of the second threaded hole in the first biodegradable base, configured to allow a device with the diameter and threading to mate with the first hole in the first biodegradable base to pass through unobstructed; and
   a biodegradable connector for connecting the first surface of the first biodegradable base with the first surface of the second biodegradable base, the biodegradable connector defined to compress the first biodegradable base against the second biodegradable base using an external force,
      wherein the length of the connector is sufficient to connect to the first biodegradable base and the second biodegradable base while allowing enough space to maintain a predefined gap substantially equal to the tissue thickness between the first surface of the biodegradable base and the first surface of the second biodegradable base, and the biodegradable connector having an unthreaded hole substantially through the middle of the same size and alignment as the unthreaded hole in the second biodegradable base, allowing a device with the diameter and threading to mate with the second threaded hole in the first biodegradable base to pass through unobstructed.

17. The biodegradable implantable device in claim 16, wherein the biodegradable connector comprises a ratcheting mechanism.

18. The biodegradable implantable device in claim 16, wherein the biodegradable connector comprises a locking or clasping mechanism.

* * * * *